United States Patent [19]

Huang et al.

[11] Patent Number: 5,874,606

[45] Date of Patent: Feb. 23, 1999

[54] PROCESS FOR MAKING O-ARYLBENZONITRILES

[75] Inventors: Bao-Guo Huang, Cheektowaga; David Y. Tang, East Amherst, both of N.Y.

[73] Assignee: Occidental Chemical Corporation, Niagara Falls, N.Y.

[21] Appl. No.: 52,556

[22] Filed: Mar. 31, 1998

[51] Int. Cl.$^6$ ............................................. C07C 255/00
[52] U.S. Cl. ............................................. 558/411
[58] Field of Search ............................................. 558/411

[56] References Cited

U.S. PATENT DOCUMENTS

| | | | |
|---|---|---|---|
| 5,288,895 | 2/1994 | Bousset et al. | 558/378 |
| 5,380,910 | 1/1995 | Kageyama | 558/359 |

FOREIGN PATENT DOCUMENTS

| | | |
|---|---|---|
| 08109143 | 4/1996 | Japan . |
| 08231454 | 9/1996 | Japan . |
| WO9730970 | 8/1997 | WIPO . |

OTHER PUBLICATIONS

Cram, D.J., et al, "Host–Guest Complexation: 29 Expanded Hemispherands", JACS, 106(11), 3287–3292, 1984.

Katz, H.E., "Chelate and Macrocycle Effects in the 2,2'-Bipyridine N,N'-Dioxide complexation of Alkyltin Trichlorides", JOC, 50, 2086–2091, 1985.

*Primary Examiner*—Johann Richter
*Assistant Examiner*—Joseph Murray
*Attorney, Agent, or Firm*—Richard D. Fuerle; Anne E. Brookes

[57] ABSTRACT

Disclosed is a method of making an o-arylbenzonitrile. A mixture is prepared of o-chlorobenzonitrile and about 1.0 to about 2.0 equivalents per equivalent of o-chlorobenzonitrile of a substituted phenylmagnesium halide in about 5 to about 30 mL per gram of o-chlorobenzonitrile of a solvent system of an ethereal solvent and N-methyl pyrrolidinone. The o-chlorobenzonitrile is reacted with the substituted phenylmagnesium halide at a temperature of about 10-° to about 25° C.

20 Claims, No Drawings

PROCESS FOR MAKING O-ARYLBENZONITRILES

BACKGROUND OF THE INVENTION

This invention relates to a process for making o-aryl benzonitrile by reacting o-chlorobenzonitrile (OCBN) with a substituted phenylmagnesium halide. In particular, it relates to a method of making o-tolylbenzonitrile (OTBN) by reacting OCBN with p-tolylmagnesium chloride in the presence of a nickel catalyst, an ethereal solvent, and N-methylpyrrolidinone (NMP) as a cosolvent.

OTBN is a key intermediate for the synthesis of antihypertensive drugs. Various methods have been reported in the literature for making OTBN. As described in patents DE 19607135, JP 08109143, and EP 566468, OTBN can be made by reacting o-bromobenzonitrile (OBBN) with p-tolylmagnesium bromide in the presence of a Pd, Ni, or Mn catalyst. While those processes produce OTBN with a good yield, the starting materials (both OBBN and p-bromotoluene) are very expensive. In JP 08231454, OCBN is reacted with p-tolylmagnesium chloride in the presence of a zinc salt and an amine to give OTBN.

SUMMARY OF THE INVENTION

We have discovered that OTBN and related o-arylbenzonitriles can be prepared by reacting low cost, commercially available OCBN with a substituted phenylmagnesium halide in the presence of a nickel catalyst, an ethereal solvent, and NMP as a cosolvent. While OCBN is less reactive than the expensive OBBN, we have nevertheless been able to obtain OTBN with a yield of about 90% using the method of this invention.

DESCRIPTION OF THE PREFERRED EMBODIMENTS

In the process of this invention, OCBN is reacted with a substituted phenylmagnesium halide having the general formula:

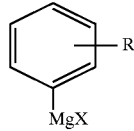

where R is alkyl or alkoxy from $C_1$ to $C_4$ and X is chlorine, bromine, or iodine. Preferably, R is alkyl and most preferably methyl, and preferably R is in the para position because the products, such as OTBN, are commercially important. Also, X is preferably chlorine as that compound is easier to make. Examples of suitable substituted phenylmagnesium halides include p-tolylmagnesium chloride, o-tolylmagnesium chloride, m-tolylmagnesium chloride, and p-tolylmagnesium bromide. The preferred substituted phenylmagnesium halide is p-tolylmagnesium chloride because it is commercially available and has been found to work well. The amount of substituted phenylmagnesium halide should be about 1.0 to about 2.0 equivalents per equivalent of OCBN as less is ineffective and more is unnecessary; the preferred amount of substituted phenylmagnesium halide is about 1.0 to about 1.2 equivalents.

About 0.5 to 10 mole % (based on moles of OCBN) of a nickel catalyst is used in the reaction. Less catalyst is ineffective and more catalyst is unnecessary. The preferred amount of catalyst is about 2 to about 5 mole %, based on the moles of OCBN. The catalyst has the general formula $NiL_mX_n$, where L is an organic ligand bonded to the nickel atom, X is chlorine, bromine, or iodine, m is 0 to 4, and n is 0 to 2; X is preferably chlorine as those catalysts are commercially available or are easier to make. Some of the catalysts are commercially available and, in some cases, the catalyst can be prepared in situ by reacting $NiX_n$ with the organic ligand. Examples of these ligands include triphenylphosphine, tricyclohexylphosphine, tributylphosphine, tributylphosphite, and tri(isopropylphosphite); the preferred ligand is triphenylphosphine. Examples of suitable catalysts include dichlorobis(triphenylphosphine)nickel, $Ni(PPh_3)_2Cl_2$, (TPPN), where "Ph" is phenyl, dichlorobis(tributylphosphine)nickel, nickel (II) chloride and triphenylphosphine, nickel(II) chloride and tricyclohexylphosphine, nickel(II) acetylacetonate, tetrakis (triphenylphosphine)nickel(0), and tetrakis (triphenylphosphite)nickel(0), the preferred catalyst is TPPN because it has been found to work well and is readily accessible.

About 5 to about 30 pbw mL per gram of OCBN of a solvent system which comprises an ethereal solvent (i.e., a solvent that contains a C-O-C group) and NMP cosolvent are present during the reaction. If less of the solvent system is used more unwanted byproducts may be produced and more of the solvent system is unnecessary. The preferred amount of combined ethereal solvent and NMP cosolvent is about 10 to 20 mL per gram of OCBN. Examples of suitable ethereal solvents include tetrahydrofuran (THF), methyl t-butylether (MTBE), hydroxyethyl acetate glycol monoacetate, diethyl ether, diethylene glycol diethyl ether, 1,2-dimethoxy ethane, diethylene glycol dimethyl ether, 1,2-bis(2-methoxyethoxy) ethane, bis[2-(2-methoxyethoxy)ethyl]ether, diethyleneglycol dimethyl ether, and diethylene glycol ether. The preferred ethereal solvent is THF because it has been found to work well. About 2 to about 12 molar equivalents of NMP should be used per equivalent of OCBN. Less NMP is ineffective and more NMP is unnecessary. Preferably, about 6 to about 8 equivalents of NMP should be used.

The reaction can be performed in various ways, but is preferably performed by adding the substituted phenylmagnesium halide to a solution of the OCBN, the nickel catalyst, the solvent, and the NMP cosolvent at temperatures of between –10° and 25° C. for about 1 to about 10 hours. A temperature of about –10° to about 10° C. is preferred. The reaction is complete when OCBN is no longer detected by gas chromatography (GC).

The following examples further illustrate this invention.

EXAMPLE 1

A mixture of OCBN (6.87 g, 50 mmol), TPPN (1.64 g, 2.5 mmol, 5 mol %) in THF (30 mL) and NMP (30 mL) were placed in a three-necked, round-bottomed flask. A solution of p-tolylmagnesium chloride (2.04M, 29.4 mL, 60 mmol, 1.2 equiv.) in THF was added dropwise, while maintaining the temperature at 5° to 10° C. The addition required about 30 min. The stirring was continued at that temperature for 3 h. The mixture was diluted with ethyl acetate (100 mL) and hydrolyzed at the same temperature with 2N hydrochloric acid. The aqueous phase was extracted with ethyl acetate (2×50 mL). The combined organic phase was dried over magnesium sulfate and concentrated to give a brown syrup, which was purified by column chromatography followed by recrystallization from ethanol. The desired OTBN product was obtained in the form of a white crystal (7.72 g, 80%). M.p.: 52°–53° C.

EXAMPLE 2

Example 1 was repeated, starting from 4.13 g (30 mmol) of OCBN, 981 mg (5 mol %) of TPPN, and 16.2 mL of p-tolylmagnesium chloride (33.0 mmol, 1.1 equiv.) in THF (6 mL) and NMP (22.5 mL). A GC yield of 90% OTBN was obtained based on internal standard analysis (tridecane).

EXAMPLE 3

Example 1 was repeated, starting from 4.13 g (30 mmol) of OCBN, 392.6 mg (2 mol %) of TPPN, and 16.2 mL of p-tolylmagnesium chloride (33.0 mmol, 1.1 equiv.) in THF (14 mL) and NMP (15 mL). A GC yield of 55% OTBN was obtained based on internal standard analysis (tridecane).

EXAMPLE 4

Example 1 was repeated, starting from 4.13 g (30 mmol) of OCBN, 981 mg (5 mol %) of TPPN, and 16.2 mL of p-tolylmagnesium chloride (33.0 mmol, 1.1 equiv.) in THF (14 mL) and NMP (15 mL). A GC yield of 82% OTBN was obtained, based on internal standard analysis (tridecane).

EXAMPLE 5

Example 1 was repeated, starting from 200 g (1.45 mol) of OCBN, 47.0 g (5 mol %) of TPPN and 855 mL of p-tolylmagnesium chloride (1.74 mol, 1.2 equiv.) in THF (145 mL) and NMP (500 mL). A GC yield of 89% OTBN was obtained based on internal standard analysis (tridecane).

EXAMPLE 6

Example 1 was repeated, starting from 4.13 g (30 mmol) of OCBN, 196 mg (5 mol %) of TPPN (787 mg, 10 mol%) and 16.2 mL of p-tolylmagnesium chloride (33.0 mmol, 1.1 equiv.) in THF (13.8 mL) and NMP (15 mL). A GC yield of 74% OTBN was obtained, based on internal standard analysis (tridecane).

EXAMPLE 7—Comparative

The same process was used as that of Example 1, starting from 4.13 g (30 mmol) of OCBN, 981 mg (5 mol %) of TPPN, and 16.2 mL of p-tolylmagnesium chloride (33.0 mmol, 1.1 equiv.) in THF (28.8 mL) at room temperature. After 5 h, the GC yield of 15% OTBN was obtained based on internal standard analysis (tridecane). This example shows that the yield drops precipitously when NMP is not present.

We claim:

1. A method of making an o-arylbenzonitrile comprising
   (A) preparing a mixture of
   (1) o-chlorobenzonitrile;
   (2) about 1.0 to about 2.0 equivalents per equivalent of said o-chlorobenzonitrile of a substituted phenylmagnesium halide having the general formula

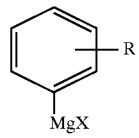

where R is alkyl or alkoxy from $C_1$ to $C_4$ and X is chlorine, bromine, or iodine
   3) about 5 to about 30 mL per gram of said o-chlorobenzonitrile of a solvent system which comprises N-methyl pyrrolidinone and an ethereal solvent in a ratio of about 2 to about 12 equivalents of said N-methyl pyrrolidinone per equivalent of said o-chlorobenzonitrile; and
   (4) about 0.5 to about 10 mole %, based on moles of said o-chlorobenzonitrile, of a nickel catalyst having the general formula $NiL_mX_n$, where L is an organic ligand bonded to the nickel atom, X is chlorine, bromine, or iodine, m is 0 to 4, and n is 0 to 2; and
   (B) reacting said o-chlorobenzonitrile with said substituted phenylmagnesium halide at a temperature of about –10° to about 25° C.

2. A method according to claim 1 wherein R is alkyl.

3. A method according to claim 2 wherein R is methyl.

4. A method according to claim 1 wherein R is the para position.

5. A method according to claim 1 wherein X in said substituted phenylmagnesium halide is chlorine.

6. A method according to claim 1 wherein said substituted phenylmagnesium halide is p-tolylmagnesium chloride.

7. A method according to claim 1 wherein the nickel in said nickel catalyst is in the II oxidation state.

8. A method according to claim 1 wherein the nickel in said nickel catalyst is in the 0 oxidation state.

9. A method according to claim 1 wherein m is 2 and both L's are triphenylphosphine.

10. A method according to claim 1 wherein X in said nickel catalyst is chlorine.

11. A method according to claim 10 wherein said catalyst is dichlorobis(triphenylphosphine) nickel.

12. A method according to claim 1 wherein said ethereal solvent is tetrahydrofuran.

13. A method of making an o-arylbenzonitrile comprising
   (A) preparing a solution of
   (1) o-chlorobenzonitrile;
   (2) about 2 to about 5 mole % of a nickel catalyst selected from the group consisting of dichlorobis(triphenylphosphine)nickel, dichlorobis(tributylphosphine)nickel, nickel(II) chloride and triphenylphosphine, nickel(II) chloride and tricyclohexylphosphine, nickel(II) acetylacetonate, tetrakis(triphenylphosphine)nickel(0), and tetrakis(triphenylphosphite)nickel(0); and
   (3) about 10 to about 20 mL per gram of o-chlorobenzonitrile of a solvent system which comprises
      (a) an ethereal solvent selected from the group consisting of tetrahydrofuran, methyl t-butylether, hydroxyethyl acetate glycol monoacetate, diethyl ether, diethylene glycol diethyl ether, 1,2-dimethoxy ethane, diethylene glycol dimethyl ether, 1,2-bis(2-methoxyethoxy) ethane, bis[2-(2-methoxyethoxy)ethyl]ether, diethyleneglycol dimethyl ether, and diethylene glycol ether; and
      (b) about 6 to about 8 equivalents of N-methylpyrrolidinone, per equivalent of said 0-chlorobenzonitrile;
   (B) mixing into said solution about 1.0 to about 1.2 equivalents per equivalent of said o-chlorobenzonitrile of a phenylmagnesium chloride having the general formula

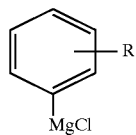

where R is alkyl or alkoxy from $C_1$ to $C_4$; and (C) reacting said o-chlorobenzonitrile with said substituted phenylmagnesium chloride at a temperature of about −10° to about 25° C.

14. A method according to claim 13 wherein R is alkyl in the para position.

15. A method according to claim 13 wherein the nickel in said nickel catalyst is in the II oxidation state.

16. A method according to claim 13 wherein m is 2 and both L's are triphenylphosphine.

17. A method according to claim 13 wherein said nickel catalyst is dichlorobis(triphenyl)phosphine nickel.

18. A method according to claim 13 wherein said ethereal solvent is tetrahydrofuran.

19. A method of making o-tolylbenzonitrile comprising
   (A) preparing a solution of
   (1) o-chlorobenzonitrile;
   (2) about 2 to about 5 mole % of dichlorobis(triphenyl)phosphine nickel; and
   (3) about 10 to about 20 pbw per pbw of o-chlorobenzonitrile of a solvent system which comprises an ethereal solvent selected from the group consisting of tetrahydrofuran, methyl t-butylether, hydroxyethyl acetate glycol monoacetate, diethyl ether, diethylene glycol diethyl ether, 1,2-dimethoxy ethane, diethylene glycol dimethyl ether, 1,2bis(2-methoxyethoxy) ethane, bis[2-(2-methoxyethoxy)ethyl]ether, diethyleneglycol dimethyl ether, and diethylene glycol ether and about 6 to about 8 equivalents of N-methylpyrrolidinone per equivalent of said o-chlorobenzonitrile; and (B) mixing into said solution about 1.0 to about 1.2 equivalents per equivalent of said o-chlorobenzonitrile of p-tolylmagnesium chloride; and (C) reacting said o-chlorobenzonitrile with said p-tolylmagnesium chloride at a temperature of about −10° to about 25° C.

20. A method according to claim 19 wherein said ethereal solvent is tetrahydrofuran.

* * * * *